(12) United States Patent
Wham

(10) Patent No.: US 9,119,624 B2
(45) Date of Patent: Sep. 1, 2015

(54) ARC BASED ADAPTIVE CONTROL SYSTEM FOR AN ELECTROSURGICAL UNIT

(71) Applicant: Covidien AG, Neuhausen am Rheinfall (CH)

(72) Inventor: Robert H. Wham, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 106 days.

(21) Appl. No.: 14/048,946

(22) Filed: Oct. 8, 2013

(65) Prior Publication Data

US 2014/0039490 A1 Feb. 6, 2014

Related U.S. Application Data

(63) Continuation of application No. 12/637,153, filed on Dec. 14, 2009, now Pat. No. 8,556,890, which is a continuation of application No. 11/409,574, filed on Apr. 24, 2006, now Pat. No. 7,651,492.

(51) Int. Cl.
*A61B 18/10* (2006.01)
*A61B 18/12* (2006.01)
*A61B 18/00* (2006.01)

(52) U.S. Cl.
CPC ... *A61B 18/1206* (2013.01); *A61B 2018/00726* (2013.01); *A61B 2018/00875* (2013.01); *A61B 2018/1213* (2013.01)

(58) Field of Classification Search
CPC ............ A61B 2018/00755; A61B 2018/00726; A61B 2018/00767; A61B 2018/00875; A61B 2018/00898
See application file for complete search history.

(56) References Cited

U.S. PATENT DOCUMENTS

| | | | |
|---|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

U.S. Appl. No. 10/406,690, filed Apr. 3, 2003, Robert J. Behnke, II.

(Continued)

*Primary Examiner* — Ronald Hupczey, Jr.

(57) ABSTRACT

A system and method for performing electrosurgical procedures are disclosed. The system includes an electrosurgical generator adapted to supply electrosurgical energy to tissue in form of one or more electrosurgical waveforms having a crest factor and a duty cycle. The system also includes sensor circuitry adapted to measure impedance and to obtain one or more measured impedance signals. The sensor circuitry is further adapted to generate one or more arc detection signals upon detecting an arcing condition§. The system further includes a controller adapted to generate one or more target control signals as a function of the measured impedance signals and to adjust output of the electrosurgical generator based on the arc detection signal. An electrosurgical instrument is also included having one or more active electrodes adapted to apply electrosurgical energy to tissue.

14 Claims, 2 Drawing Sheets

(56) References Cited

U.S. PATENT DOCUMENTS

| | | |
|---|---|---|
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko et al. |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan, Sr. et al. |
| 4,903,696 A | 2/1990 | Stasz et al. |

(56) References Cited

U.S. PATENT DOCUMENTS

| | | |
|---|---|---|
| 4,907,589 A | 3/1990 | Cosman |
| 4,922,210 A | 5/1990 | Flachenecker et al. |
| 4,925,089 A | 5/1990 | Chaparro et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,067,953 A | 11/1991 | Feucht |
| 5,075,839 A | 12/1991 | Fisher et al. |
| 5,087,257 A | 2/1992 | Farin et al. |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker et al. |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke et al. |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,234,427 A | 8/1993 | Ohtomo et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin et al. |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A * | 4/1994 | Rosar et al. .................. 606/34 |
| 5,300,070 A | 4/1994 | Gentelia et al. |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman et al. |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,369,567 A | 11/1994 | Furuta et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson et al. |
| 5,383,876 A | 1/1995 | Nardella |
| 5,383,917 A | 1/1995 | Desai et al. |
| 5,385,148 A | 1/1995 | Lesh et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson et al. |
| 5,433,739 A | 7/1995 | Sluijter et al. |
| 5,436,566 A | 7/1995 | Thompson et al. |
| 5,438,302 A | 8/1995 | Goble |
| 5,443,463 A | 8/1995 | Stern et al. |
| 5,445,635 A | 8/1995 | Denen et al. |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,485,312 A | 1/1996 | Horner et al. |
| 5,496,312 A | 3/1996 | Klicek |
| 5,496,313 A | 3/1996 | Gentelia et al. |
| 5,496,314 A | 3/1996 | Eggers |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,541,376 A | 7/1996 | Ladtkow et al. |
| 5,545,161 A | 8/1996 | Imran |
| 5,556,396 A | 9/1996 | Cohen et al. |
| 5,558,671 A | 9/1996 | Yates |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |

(56) References Cited

U.S. PATENT DOCUMENTS

| | | |
|---|---|---|
| 5,660,567 A | 8/1997 | Nierlich et al. |
| 5,664,953 A | 9/1997 | Reylek |
| 5,674,217 A | 10/1997 | Wahlstrom et al. |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern et al. |
| 5,766,153 A | 6/1998 | Eggers et al. |
| 5,766,165 A | 6/1998 | Gentelia et al. |
| 5,769,847 A | 6/1998 | Panescu et al. |
| 5,772,659 A | 6/1998 | Becker et al. |
| 5,788,688 A | 8/1998 | Bauer et al. |
| 5,792,138 A | 8/1998 | Shipp |
| 5,797,902 A | 8/1998 | Netherly |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell et al. |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling et al. |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,959,253 A | 9/1999 | Shinchi |
| 5,961,344 A | 10/1999 | Rosales et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,017,354 A | 1/2000 | Culp et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,045,527 A | 4/2000 | Appelbaum et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,090,123 A | 7/2000 | Culp et al. |
| 6,093,186 A | 7/2000 | Goble |
| 6,102,497 A | 8/2000 | Ehr et al. |
| 6,102,907 A | 8/2000 | Smethers et al. |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven et al. |
| 6,123,701 A | 9/2000 | Nezhat |
| 6,123,702 A | 9/2000 | Swanson et al. |
| 6,132,429 A | 10/2000 | Baker |
| 6,142,992 A | 11/2000 | Cheng et al. |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,171,304 B1 | 1/2001 | Netherly et al. |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek et al. |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman et al. |
| 6,241,723 B1 | 6/2001 | Heim et al. |
| 6,241,725 B1 | 6/2001 | Cosman |
| 6,243,654 B1 | 6/2001 | Johnson et al. |

(56) References Cited

U.S. PATENT DOCUMENTS

| | | | |
|---|---|---|---|
| 6,245,061 B1 | 6/2001 | Panescu et al. | |
| 6,245,063 B1 | 6/2001 | Uphoff | |
| 6,245,065 B1 | 6/2001 | Panescu et al. | |
| 6,246,912 B1 | 6/2001 | Sluijter et al. | |
| 6,251,106 B1 | 6/2001 | Becker et al. | |
| 6,254,422 B1 | 7/2001 | Feye-Hohmann | |
| 6,258,085 B1 | 7/2001 | Eggleston | |
| 6,261,285 B1 | 7/2001 | Novak et al. | |
| 6,261,286 B1 | 7/2001 | Goble et al. | |
| 6,267,760 B1 | 7/2001 | Swanson | |
| 6,273,886 B1 | 8/2001 | Edwards et al. | |
| 6,275,786 B1 | 8/2001 | Daners | |
| 6,293,941 B1 | 9/2001 | Strul et al. | |
| 6,293,942 B1 | 9/2001 | Goble et al. | |
| 6,293,943 B1 | 9/2001 | Panescu et al. | |
| 6,296,636 B1 | 10/2001 | Cheng et al. | |
| 6,306,131 B1 | 10/2001 | Hareyama et al. | |
| 6,306,134 B1 | 10/2001 | Goble et al. | |
| 6,309,386 B1 | 10/2001 | Bek | |
| 6,322,558 B1 | 11/2001 | Taylor et al. | |
| 6,325,799 B1 | 12/2001 | Goble | |
| 6,329,778 B1 | 12/2001 | Culp et al. | |
| 6,337,998 B1 | 1/2002 | Behl et al. | |
| 6,338,657 B1 | 1/2002 | Harper et al. | |
| 6,350,262 B1 | 2/2002 | Ashley | |
| 6,358,245 B1 | 3/2002 | Edwards et al. | |
| 6,364,877 B1 | 4/2002 | Goble et al. | |
| 6,371,963 B1 | 4/2002 | Nishtala et al. | |
| 6,383,183 B1 | 5/2002 | Sekino et al. | |
| 6,391,024 B1 | 5/2002 | Sun et al. | |
| 6,398,779 B1 | 6/2002 | Buysse et al. | |
| 6,398,781 B1 | 6/2002 | Goble et al. | |
| 6,402,741 B1 | 6/2002 | Keppel et al. | |
| 6,402,742 B1 | 6/2002 | Blewett et al. | |
| 6,402,743 B1 | 6/2002 | Orszulak et al. | |
| 6,402,748 B1 | 6/2002 | Schoenman et al. | |
| 6,409,722 B1 * | 6/2002 | Hoey et al. | 606/34 |
| 6,413,256 B1 | 7/2002 | Truckai et al. | |
| 6,416,509 B1 | 7/2002 | Goble et al. | |
| 6,422,896 B2 | 7/2002 | Aoki et al. | |
| 6,423,057 B1 | 7/2002 | He et al. | |
| 6,426,886 B1 | 7/2002 | Goder | |
| 6,428,537 B1 | 8/2002 | Swanson et al. | |
| 6,436,096 B1 | 8/2002 | Hareyama | |
| 6,440,157 B1 | 8/2002 | Shigezawa et al. | |
| 6,451,015 B1 | 9/2002 | Rittman, III et al. | |
| 6,454,594 B2 | 9/2002 | Sawayanagi | |
| 6,458,121 B1 | 10/2002 | Rosenstock et al. | |
| 6,458,122 B1 | 10/2002 | Pozzato | |
| 6,464,689 B1 | 10/2002 | Qin et al. | |
| 6,464,696 B1 | 10/2002 | Oyama et al. | |
| 6,468,270 B1 | 10/2002 | Hovda et al. | |
| 6,468,273 B1 | 10/2002 | Leveen et al. | |
| 6,482,201 B1 | 11/2002 | Olsen et al. | |
| 6,488,678 B2 | 12/2002 | Sherman | |
| 6,494,880 B1 | 12/2002 | Swanson et al. | |
| 6,497,659 B1 | 12/2002 | Rafert | |
| 6,498,466 B1 | 12/2002 | Edwards | |
| 6,506,189 B1 | 1/2003 | Rittman, III et al. | |
| 6,508,815 B1 | 1/2003 | Strul et al. | |
| 6,511,476 B2 | 1/2003 | Hareyama | |
| 6,511,478 B1 | 1/2003 | Burnside et al. | |
| 6,517,538 B1 | 2/2003 | Jacob et al. | |
| 6,522,931 B2 | 2/2003 | Manker et al. | |
| 6,524,308 B1 | 2/2003 | Muller et al. | |
| 6,537,272 B2 | 3/2003 | Christopherson et al. | |
| 6,544,260 B1 | 4/2003 | Markel et al. | |
| 6,546,270 B1 | 4/2003 | Goldin et al. | |
| 6,547,786 B1 | 4/2003 | Goble | |
| 6,557,559 B1 | 5/2003 | Eggers et al. | |
| 6,558,376 B2 | 5/2003 | Bishop | |
| 6,558,377 B2 | 5/2003 | Lee et al. | |
| 6,560,470 B1 | 5/2003 | Pologe | |
| 6,562,037 B2 | 5/2003 | Paton et al. | |
| 6,565,559 B2 | 5/2003 | Eggleston | |
| 6,565,562 B1 | 5/2003 | Shah et al. | |
| 6,575,969 B1 | 6/2003 | Rittman, III et al. | |
| 6,578,579 B2 | 6/2003 | Burnside et al. | |
| 6,579,288 B1 | 6/2003 | Swanson et al. | |
| 6,582,427 B1 | 6/2003 | Goble et al. | |
| 6,602,243 B2 | 8/2003 | Noda | |
| 6,602,252 B2 | 8/2003 | Mollenauer | |
| 6,611,793 B1 | 8/2003 | Burnside et al. | |
| 6,620,157 B1 | 9/2003 | Dabney et al. | |
| 6,620,189 B1 | 9/2003 | Machold et al. | |
| 6,623,423 B2 | 9/2003 | Sakurai et al. | |
| 6,626,901 B1 | 9/2003 | Treat et al. | |
| 6,629,973 B1 | 10/2003 | Wårdell et al. | |
| 6,632,193 B1 | 10/2003 | Davison et al. | |
| 6,635,056 B2 | 10/2003 | Kadhiresan et al. | |
| 6,635,057 B2 | 10/2003 | Harano et al. | |
| 6,645,198 B1 | 11/2003 | Bommannan et al. | |
| 6,648,883 B2 | 11/2003 | Francischelli et al. | |
| 6,651,669 B1 | 11/2003 | Burnside | |
| 6,652,513 B2 | 11/2003 | Panescu et al. | |
| 6,652,514 B2 | 11/2003 | Ellman et al. | |
| 6,653,569 B1 | 11/2003 | Sung | |
| 6,656,177 B2 | 12/2003 | Truckai et al. | |
| 6,663,623 B1 | 12/2003 | Oyama et al. | |
| 6,663,624 B2 | 12/2003 | Edwards et al. | |
| 6,663,627 B2 | 12/2003 | Francischelli et al. | |
| 6,666,860 B1 | 12/2003 | Takahashi | |
| 6,672,151 B1 | 1/2004 | Schultz et al. | |
| 6,679,875 B2 | 1/2004 | Honda et al. | |
| 6,682,527 B2 | 1/2004 | Strul | |
| 6,685,700 B2 | 2/2004 | Behl et al. | |
| 6,685,701 B2 | 2/2004 | Orszulak et al. | |
| 6,685,703 B2 | 2/2004 | Pearson et al. | |
| 6,689,131 B2 | 2/2004 | McClurken | |
| 6,692,489 B1 | 2/2004 | Heim et al. | |
| 6,693,782 B1 | 2/2004 | Lash | |
| 6,695,837 B2 | 2/2004 | Howell | |
| 6,696,844 B2 | 2/2004 | Wong et al. | |
| 6,712,813 B2 | 3/2004 | Ellman et al. | |
| 6,730,078 B2 | 5/2004 | Simpson et al. | |
| 6,730,079 B2 | 5/2004 | Lovewell | |
| 6,730,080 B2 | 5/2004 | Harano et al. | |
| 6,733,495 B1 | 5/2004 | Bek et al. | |
| 6,733,498 B2 | 5/2004 | Paton et al. | |
| 6,740,079 B1 | 5/2004 | Eggers et al. | |
| 6,740,085 B2 | 5/2004 | Hareyama et al. | |
| 6,743,225 B2 | 6/2004 | Sanchez et al. | |
| 6,746,284 B1 | 6/2004 | Spink, Jr. | |
| 6,749,624 B2 | 6/2004 | Knowlton | |
| 6,755,825 B2 | 6/2004 | Shoenman et al. | |
| 6,758,846 B2 | 7/2004 | Goble et al. | |
| 6,761,716 B2 | 7/2004 | Kadhiresan et al. | |
| 6,783,523 B2 | 8/2004 | Qin et al. | |
| 6,784,405 B2 | 8/2004 | Flugstad et al. | |
| 6,786,905 B2 | 9/2004 | Swanson et al. | |
| 6,790,206 B2 | 9/2004 | Panescu | |
| 6,792,390 B1 | 9/2004 | Burnside et al. | |
| 6,796,980 B2 | 9/2004 | Hall | |
| 6,796,981 B2 | 9/2004 | Wham et al. | |
| 6,809,508 B2 | 10/2004 | Donofrio | |
| 6,818,000 B2 | 11/2004 | Muller et al. | |
| 6,824,539 B2 | 11/2004 | Novak | |
| 6,830,569 B2 | 12/2004 | Thompson et al. | |
| 6,837,888 B2 | 1/2005 | Ciarrocca et al. | |
| 6,843,682 B2 | 1/2005 | Matsuda et al. | |
| 6,843,789 B2 | 1/2005 | Goble | |
| 6,849,073 B2 | 2/2005 | Hoey et al. | |
| 6,855,141 B2 | 2/2005 | Lovewell | |
| 6,855,142 B2 | 2/2005 | Harano et al. | |
| 6,860,881 B2 | 3/2005 | Sturm et al. | |
| 6,864,686 B2 | 3/2005 | Novak et al. | |
| 6,875,210 B2 | 4/2005 | Refior et al. | |
| 6,890,331 B2 | 5/2005 | Kristensen | |
| 6,893,435 B2 * | 5/2005 | Goble | 606/41 |
| 6,899,538 B2 | 5/2005 | Matoba | |
| 6,923,804 B2 | 8/2005 | Eggers et al. | |
| 6,929,641 B2 | 8/2005 | Goble et al. | |
| 6,936,047 B2 | 8/2005 | Nasab et al. | |
| 6,939,344 B2 | 9/2005 | Kreindel | |

(56) References Cited

U.S. PATENT DOCUMENTS

| | | |
|---|---|---|
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,582,084 B2 | 9/2009 | Swanson et al. |
| 7,651,492 B2 | 1/2010 | Wham |
| 7,956,620 B2 | 6/2011 | Gilbert |
| 8,152,802 B2 | 4/2012 | Podhajsky et al. |
| 8,162,932 B2 | 4/2012 | Podhajsky et al. |
| 8,167,875 B2 | 5/2012 | Podhajsky et al. |
| 8,174,267 B2 | 5/2012 | Brannan et al. |
| 8,180,433 B2 | 5/2012 | Brannan et al. |
| 8,211,100 B2 | 7/2012 | Podhajsky et al. |
| 8,226,639 B2 | 7/2012 | Podhajsky et al. |
| 8,231,553 B2 | 7/2012 | Joseph et al. |
| 8,235,917 B2 | 8/2012 | Joseph et al. |
| 8,242,782 B2 | 8/2012 | Brannan et al. |
| 8,248,075 B2 | 8/2012 | Brannan et al. |
| 8,262,652 B2 | 9/2012 | Podhajsky |
| 8,287,527 B2 | 10/2012 | Brannan et al. |
| 8,287,529 B2 | 10/2012 | Orszulak |
| 8,333,759 B2 | 12/2012 | Podhajsky |
| 8,346,370 B2 | 1/2013 | Haley et al. |
| 8,377,053 B2 | 2/2013 | Orszulak |
| 8,377,054 B2 | 2/2013 | Gilbert |
| 8,382,751 B2 | 2/2013 | Gilbert et al. |
| 8,403,924 B2 | 3/2013 | Behnke et al. |
| 8,556,890 B2 | 10/2013 | Wham |
| 8,652,125 B2 | 2/2014 | Keller |
| 2002/0029036 A1 | 3/2002 | Goble et al. |
| 2003/0073989 A1 | 4/2003 | Hoey et al. |
| 2003/0181898 A1 | 9/2003 | Bowers |
| 2004/0015159 A1 | 1/2004 | Slater et al. |
| 2004/0030330 A1 | 2/2004 | Brassell et al. |
| 2004/0068304 A1 | 4/2004 | Paton et al. |
| 2004/0097912 A1 | 5/2004 | Gonnering |
| 2004/0143263 A1 | 7/2004 | Schechter et al. |
| 2004/0172016 A1 | 9/2004 | Bek et al. |
| 2004/0215183 A1 | 10/2004 | Hoey et al. |
| 2004/0230189 A1 | 11/2004 | Keppel |
| 2005/0004564 A1 | 1/2005 | Wham et al. |
| 2005/0004634 A1 | 1/2005 | Ricart et al. |
| 2005/0021020 A1 | 1/2005 | Blaha |
| 2005/0109111 A1 | 5/2005 | Manlove et al. |
| 2005/0182398 A1 | 8/2005 | Paterson |
| 2005/0197659 A1 | 9/2005 | Bahney |
| 2005/0203504 A1 | 9/2005 | Wham et al. |

(56) References Cited

U.S. PATENT DOCUMENTS

| | | |
|---|---|---|
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0291178 A1 | 12/2006 | Shih |
| 2006/0293649 A1 | 12/2006 | Lorang et al. |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0203481 A1 | 8/2007 | Gregg et al. |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0082096 A1 | 4/2008 | Shores et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |
| 2009/0234350 A1 | 9/2009 | Behnke et al. |
| 2009/0237169 A1 | 9/2009 | Orszulak |
| 2009/0248003 A1 | 10/2009 | Orszulak |
| 2009/0254077 A1 | 10/2009 | Craig |
| 2009/0259224 A1 | 10/2009 | Wham et al. |
| 2009/0292283 A1 | 11/2009 | Odom |
| 2010/0030210 A1 | 2/2010 | Paulus |
| 2010/0082083 A1 | 4/2010 | Brannan et al. |
| 2010/0094271 A1 | 4/2010 | Ward et al. |
| 2010/0094288 A1 | 4/2010 | Kerr |
| 2011/0028963 A1 | 2/2011 | Gilbert |
| 2011/0054460 A1 | 3/2011 | Gilbert |
| 2011/0071516 A1 | 3/2011 | Gregg |
| 2011/0112530 A1 | 5/2011 | Keller |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 | 9/1993 |
| DE | 4339049 A1 | 5/1995 |
| DE | 19506363 | 8/1996 |
| DE | 19717411 A1 | 11/1998 |
| DE | 19848540 A1 | 5/2000 |
| DE | 10 2008058737 | 4/2010 |
| EP | 0 246 350 A1 | 11/1987 |
| EP | 267403 | 5/1988 |
| EP | 296777 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 569130 A1 | 11/1993 |
| EP | 608609 A2 | 8/1994 |
| EP | 694291 A1 | 1/1996 |
| EP | 0 836 868 A2 | 4/1998 |
| EP | 0878169 A1 | 11/1998 |
| EP | 880220 A2 | 11/1998 |
| EP | 882955 | 12/1998 |
| EP | 1051948 A2 | 11/2000 |
| EP | 1053720 | 11/2000 |
| EP | 1151725 A1 | 11/2001 |
| EP | 1293171 A2 | 3/2003 |
| EP | 1472984 | 11/2004 |
| EP | 1495712 A1 | 1/2005 |
| EP | 1500378 A1 | 1/2005 |
| EP | 1535581 | 6/2005 |
| EP | 1609430 | 12/2005 |
| EP | 1366724 | 1/2006 |
| EP | 1645235 A1 | 4/2006 |
| EP | 1681026 A2 | 7/2006 |
| EP | 1707143 | 10/2006 |
| EP | 1707144 A1 | 10/2006 |
| EP | 1744354 A2 | 1/2007 |
| EP | 1776929 | 4/2007 |
| EP | 1810628 | 7/2007 |
| EP | 1810630 A1 | 7/2007 |
| EP | 1810633 A2 | 7/2007 |
| EP | 1854423 A2 | 11/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 607850 A | 9/1948 |
| GB | 702510 A | 1/1954 |
| GB | 855459 A | 11/1960 |
| GB | 902775 A | 8/1962 |
| GB | 2154881 A | 9/1985 |
| GB | 2164473 A | 3/1986 |
| GB | 2214430 A | 9/1989 |
| GB | 2358934 A | 8/2001 |
| JP | 63 005876 | 1/1988 |
| JP | 2002-065690 | 3/2002 |
| JP | 2005-185657 | 7/2005 |
| SU | 166452 | 11/1964 |
| SU | 727201 A2 | 4/1980 |
| WO | 92/06642 | 4/1992 |
| WO | 93/24066 A1 | 12/1993 |
| WO | 94/24949 A1 | 11/1994 |
| WO | 94/28809 A1 | 12/1994 |
| WO | 95/09577 A1 | 4/1995 |
| WO | 95/19148 A1 | 7/1995 |
| WO | 95/25471 A2 | 9/1995 |

(56) References Cited

FOREIGN PATENT DOCUMENTS

| | | |
|---|---|---|
| WO | 96/02180 A2 | 2/1996 |
| WO | 96/04860 A1 | 2/1996 |
| WO | 96/08794 A1 | 3/1996 |
| WO | 96/18349 A2 | 6/1996 |
| WO | 96/29946 A1 | 10/1996 |
| WO | 96/39086 A1 | 12/1996 |
| WO | 96/39914 A1 | 12/1996 |
| WO | 97/06739 A2 | 2/1997 |
| WO | 97/06740 A2 | 2/1997 |
| WO | 97/06855 A2 | 2/1997 |
| WO | 97/11648 A2 | 4/1997 |
| WO | 97/17029 A1 | 5/1997 |
| WO | 98/07378 A1 | 2/1998 |
| WO | 98/18395 A1 | 5/1998 |
| WO | 98/27880 | 7/1998 |
| WO | 99/12607 A1 | 3/1999 |
| WO | 02/00129 | 1/2002 |
| WO | 02/11634 A1 | 2/2002 |
| WO | 02/45589 A2 | 6/2002 |
| WO | 02/47565 A2 | 6/2002 |
| WO | 02/053048 A1 | 7/2002 |
| WO | 02/088128 A1 | 11/2002 |
| WO | 03/090635 A1 | 11/2003 |
| WO | 03/092520 A1 | 11/2003 |
| WO | 03/090630 A3 | 4/2004 |
| WO | 2004/028385 A1 | 4/2004 |
| WO | 2004/043240 A2 | 5/2004 |
| WO | 2004/052182 A2 | 6/2004 |
| WO | 2004/098385 A2 | 11/2004 |
| WO | 2004/103156 A2 | 12/2004 |
| WO | 2005/046496 A1 | 5/2005 |
| WO | 2005/048809 A1 | 6/2005 |
| WO | 2005/050151 A1 | 6/2005 |
| WO | 2005/060365 A2 | 7/2005 |
| WO | 2005/060849 A1 | 7/2005 |
| WO | 2006/050888 A1 | 5/2006 |
| WO | 2006/105121 A2 | 10/2006 |
| WO | WO2008/053532 | 5/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/943,518, filed Jul. 16, 2013, Orszulak et al.
U.S. Appl. No. 13/971,553, filed Aug. 20, 2013, Behnke.
U.S. Appl. No. 14/048,946, filed Oct. 3, 2013, Wham.
U.S. Appl. No. 14/058,929, filed Oct. 21, 2013, Gilbert.
U.S. Appl. No. 14/058,957, filed Oct. 21, 2013, Gilbert.
U.S. Appl. No. 14/069,534, filed Nov. 1, 2013, Digmann.
U.S. Appl. No. 14/072,312, filed Nov. 5, 2013, Wham.
U.S. Appl. No. 14/072,342, filed Nov. 5, 2013, Wham.
U.S. Appl. No. 14/073,386, filed Nov. 5, 2013, Wham.
U.S. Appl. No. 14/096,341, filed Dec. 4, 2013, Johnson.
U.S. Appl. No. 14/098,859, filed Dec. 6, 2013, Johnson.
U.S. Appl. No. 14/100,113, filed Dec. 9, 2013, Gilbert.
U.S. Appl. No. 14/144,850, filed Dec. 31, 2013, Johnston.
U.S. Appl. No. 14/147,294, filed Jan. 3, 2014, Gilbert.
U.S. Appl. No. 14/147,312, filed Jan. 3, 2014, Gilbert.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
"Electrosurgical Unit Analyzer ESU-2400 Series User Manual" Apr. 1, 2002; Retrieved from Internet: URL:http://www.bcgroupintl.com/ESU_2400/Updates/ESU-2400_UM_Rev04.pdf, pp. 6, 11, 73.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09164754.5 dated Aug. 21, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US09/46870 dated Jul. 21, 2009.
International Search Report from EP Appl. No. 11186103.5 dated Sep. 19, 2012.
Partial European Search Report from corresponding application No. EP 10 18 2005 mailed Jan. 5, 2011.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B. V. Amsterdam, NL vol. 52 No. 3.

(56) References Cited

OTHER PUBLICATIONS

Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.

* cited by examiner

ARC BASED ADAPTIVE CONTROL SYSTEM FOR AN ELECTROSURGICAL UNIT

CROSS REFERENCE TO RELATED APPLICATIONS

The present application is a continuation application of U.S. patent application Ser. No. 12/637,153 entitled "ARC BASED ADAPTIVE CONTROL SYSTEM FOR AN ELECTROSURGICAL UNIT" filed by Robert H. Wham on Dec. 14, 2009, now U.S. Pat. No. 8,556,890, which is a continuation application of U.S. patent application Ser. No. 11/409,574 entitled "ARC BASED ADAPTIVE CONTROL SYSTEM FOR AN ELECTROSURGICAL UNIT" filed by Robert H. Wham on Apr. 24, 2006, now U.S. Pat. No. 7,651,492, the entire contents of each of which are hereby incorporated by reference herein.

BACKGROUND

1. Technical Field

The present disclosure relates to electrosurgical generators. More particularly, the present disclosure relates to a system and method for controlling output of an electrosurgical generator. The electrosurgical generator includes a sensing feedback control system and an arc-based adaptive control system which adjusts output in response to arcing.

2. Background of Related Art

Energy based tissue treatment is well known in the art. Various types of energy (e.g., electrical, ultrasonic, microwave, cryo, heat, laser, etc.) are applied to tissue to achieve a desired result. Electrosurgery involves application of high radio frequency electrical current to a surgical site to cut, ablate, coagulate send or otherwise seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

It is known in the art that sensed tissue feedback may be used to control delivery of electrosurgical energy. During application of electrosurgical energy, arcing may occur during the course of treatment. Energy arcing is particularly problematic for sensed feedback control systems since the systems attempt to adjust to the rapidly occurring changes in tissue properties caused by arcing.

SUMMARY

According to one aspect of the present disclosure an electrosurgical system is disclosed. The system includes an electrosurgical generator adapted to supply electrosurgical energy to tissue in form of one or more electrosurgical waveforms having a crest factor and a duty cycle. The system also includes sensor circuitry adapted to measure impedance and to obtain one or more measured impedance signals. The sensor circuitry is further adapted to generate one or more arc detection signals upon detecting an arcing condition. The system further includes a controller adapted to generate one or more target control signals as a function of the measured impedance signals and to adjust output of the electrosurgical generator based on the arc detection signal. An electrosurgical instrument is also included having one or more active electrodes adapted to apply electrosurgical energy to tissue.

Another aspect of the present disclosure includes a method for performing an electrosurgical procedure. The method includes the steps of: supplying electrosurgical energy from an electrosurgical generator to tissue in form of one or more electrosurgical waveforms having a crest factor and a duty cycle and measuring impedance to obtain one or more measured impedance signals and generating one or more detection signal upon detecting arcing conditions. The method further includes the steps of generating one or more target control signals as a function of the measured impedance signals and adjusting output of the electrosurgical generator based on the arc detection signals.

According to a further aspect of the present disclosure an electrosurgical generator is disclosed. The generator includes an RF output stage adapted to supply electrosurgical energy to tissue in form of one or more electrosurgical waveforms having a crest factor and a duty cycle. The generator also includes sensor circuitry adapted to measure impedance and to obtain one or more measured impedance signals. The sensor circuitry is further adapted to generate one or more arc detection signals upon detecting one or more arcing conditions. The generator further includes a controller adapted to generate one or more target control signals as a function of the measured impedance signals and to adjust output of the electrosurgical generator based on the arc detection signal

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the method according to the present disclosure may be adapted to monitor use with either monopolar or bipolar electrosurgical systems.

Figure 1:
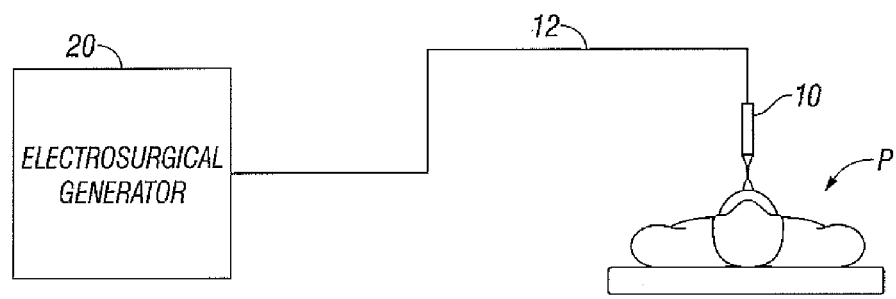
FIG. 1 is a schematic block diagram of an electrosurgical system according to the present disclosure.

FIG. 1 is a schematic illustration of an electrosurgical system according to the present disclosure. The system includes an electrosurgical instrument 10 having one or more electrodes for treating tissue of a patient P. The instrument 10 may be either a monopolar type including one or more active electrodes (e.g., electrosurgical cutting probe, ablation electrode(s), etc.) or a bipolar type including one or more active and return electrodes (e.g., electrosurgical sealing forceps). Electrosurgical RF energy is supplied to the instrument 10 by a generator 20 via a supply line 12, which is operably connected to an active output terminal, allowing the instrument 10 to coagulate, seal, ablate and/or otherwise treat tissue.

If the instrument 10 is a monopolar type instrument then energy may be returned to the generator 20 through a return electrode (not explicitly shown) which may be disposed on the patient's body. The system may also include a plurality of return electrodes which are arranged to minimize the chances of damaged tissue by maximizing the overall contact area with the patient P. In addition, the generator 20 and the monopolar return electrode may be configured for monitoring so called "tissue-to-patient" contact to insure that sufficient contact exists therebetween to further minimize chances of tissue damage.

If the instrument 10 is a bipolar type instrument, the return electrode is disposed in proximity to the active electrode (e.g., on opposing jaws of a bipolar forceps). It is also envisioned that the generator 20 may include a plurality of supply and return terminals and a corresponding number of electrode leads.

The generator 20 includes input controls (e.g., buttons, activators, switches, touch screen, etc.) for controlling the generator 20. In addition, the generator 20 may include one or more display screens for providing the surgeon with a variety of output information (e.g., intensity settings, treatment complete indicators, etc.). The controls allow the surgeon to adjust power of the RF energy, waveform, and other parameters to achieve the desired waveform suitable for a particular task (e.g., coagulating, tissue sealing, intensity setting, etc.). It is also envisioned that the instrument 10 may include a plurality of input controls which may be redundant with certain input controls of the generator 20. Placing the input controls at the instrument 10 allows for easier and faster modification of RF energy parameters during the surgical procedure without requiring interaction with the generator 20.

Figure 2:
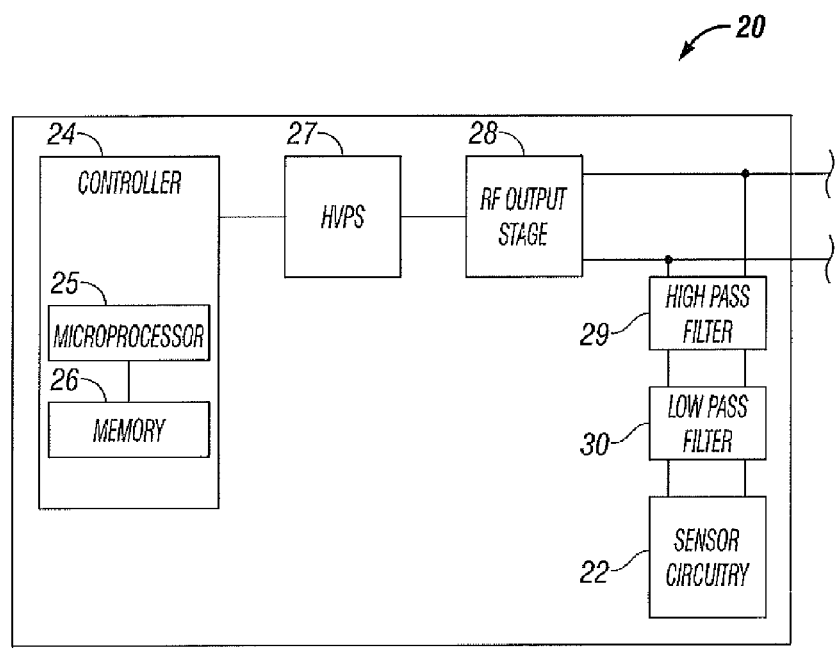
FIG. 2 is a schematic block diagram of a generator according to the present disclosure.

FIG. 2 shows a schematic block diagram of the generator 20 having a controller 24, a high voltage DC power supply 27 ("HVPS") and an RF output phase 28. The HVPS 27 provides high voltage DC power to an RF output phase 28 which then converts high voltage DC power into RF energy and delivers the high frequency RF energy to the active electrode 24. In particular, the RF output phase 28 generates sinusoidal waveforms of high frequency RF energy. The RE output phase 28 is configured to generate a plurality of waveforms having various duty cycles, peak voltages, crest factors, and other parameters. Certain types of waveforms are suitable for specific electrosurgical modes. For instance, the RF output phase 28 generates a 100% duty cycle sinusoidal waveform in cut mode, which is best suited for dissecting tissue and a 25% duty cycle waveform in coagulation mode, which is best used for cauterizing tissue to stop bleeding.

The controller 24 includes a microprocessor 25 operably connected to a memory 26 which may be volatile type memory (e.g., RAM) and/or non-volatile type memory (e.g., flash media, disk media, etc.). The microprocessor 25 includes an output port which is operably connected to the HVPS 27 and/or RF output phase 28 allowing the microprocessor 25 to control the output of the generator 20 according to either open and/or closed control loop schemes.

A closed loop control scheme or feedback control loop is provided that includes sensor circuitry 22 having one or more sensors for measuring a variety of tissue and energy properties (e.g., tissue impedance, tissue temperature, output current and/or voltage, etc.). The sensor circuitry 22 provides feedback to the controller 24. Such sensors are within the purview of those skilled in the art. The controller 24 then signals the HVPS 27 and/or RF output phase 28 which then adjust DC and/or RF power supply, respectively. The controller 24 also receives input signals from the input controls of the generator 20 or the instrument 10. The controller 24 utilizes the input signals to adjust power outputted by the generator 20 and/or performs other control functions thereon.

In particular, sensor circuitry 22 is adapted to measure tissue impedance. This is accomplished by measuring voltage and current signals and calculating corresponding impedance values as a function thereof at the sensor circuitry 22 and/or at the microprocessor 25. Power and other energy properties may also be calculated based on collected voltage and current signals. The sensed impedance measurements are used as feedback by the generator 20 for regulating the energy delivery to the tissue. Various types of impedance feedback control schemes are envisioned, such as for example, impedance matching (wherein power output is adjusted to match measured impedance to target impedance), impedance maintenance (epower is adjusted to maintain impedance), etc.

The sensor circuitry 22 obtains impedance signals and sends a corresponding target control signal that is used by the controller 24 to adjust the output of the generator 20. Since the output of the generator 20 is adjusted as a function of the measured impedance, the output of the generator 20 responds to every fluctuation in the measured impedance. While high resolution response times are desirable, certain variations in impedance may not warrant adjustments to the output of the generator 20.

During electrosurgical procedures, it is known that arcing causes rapid changes in impedance. Impedance fluctuates between arc impedance to open circuit impedance (e.g., nil). An impedance feedback control scheme that adjusts the output of the generator 20 in response to impedance changes for each arc is undesirable. If the output of the generator 20 tracks the impedance changes caused by arcing too closely, unwanted oscillation in the output may occur. The present disclosure provides an arc-based adaptive control method for mitigating oscillation and adjusting the behavior of an impedance feedback control scheme of the controller 24.

Figure 3:
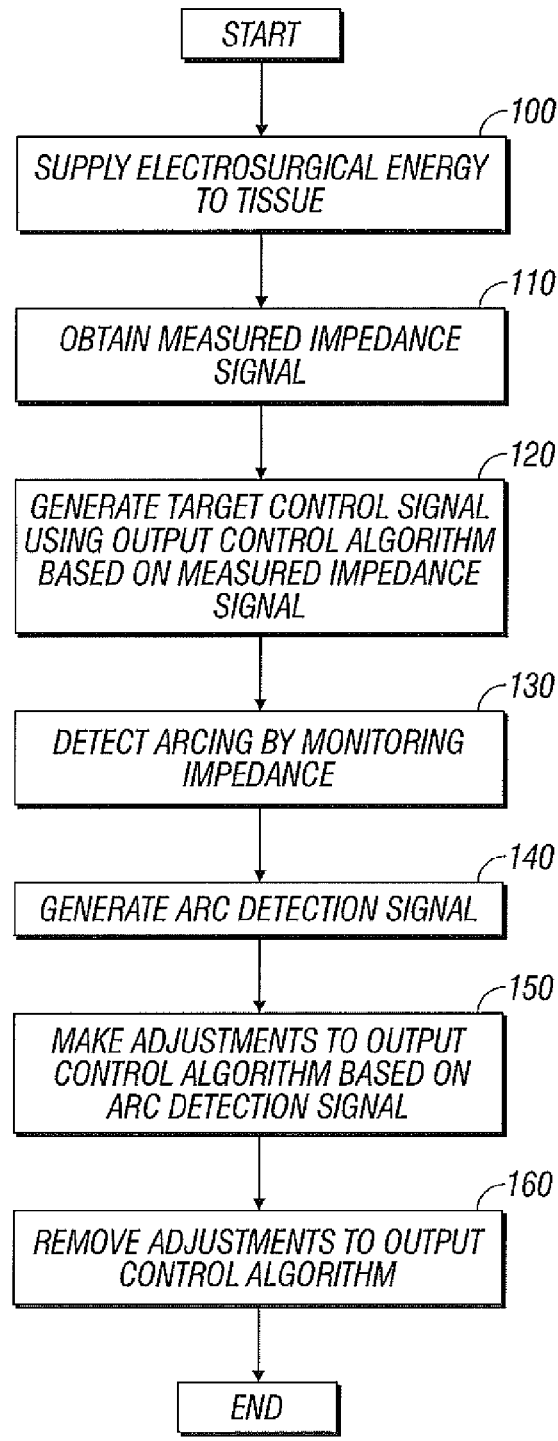
FIG. 3 is a flow diagram illustrating a method according to the present disclosure.

FIG. 3 shows an arc-based adaptive control method according to one embodiment of the present disclosure which is configured to control the output of the generator in response to monitored tissue impedance. In step 100, the instrument 10 engages the tissue and the generator 20 supplies electrosurgical energy to the tissue through the instrument 10. In step 110, during application of energy to the tissue, impedance is continually monitored by the sensor circuitry 22 and a measured impedance signal is obtained. As discussed above, the measured impedance signal is derived from voltage and current signals.

In step 120, a target control signal is generated by the controller 24 as a function of the measured impedance signal. In particular, the target control signal is generated by using output control algorithms which may operate in a wide variety of ways. For example, the algorithms may attempt to match measured impedance signal to predetermined target impedance or may simply use look-up tables containing corresponding target control signals. The output control algorithms are stored within the memory 26 and are executed by the microprocessor 26. Consequently, the target control signal is used to make appropriate adjustments to the output of the generator 20.

In step 130, arcing is detectable by monitoring for rapid repeating changes in measured impedance signal, target control signal, or voltage and current signal. Since target control signal and voltage and current signals are directly related to measured impedance signal, rapid changes in those signals are also indicative of arcing conditions. In other words, impedance correlates with arcing—low impedance is measured during an arc condition followed by high impedance when arcing stops. In step 140, an arc detection signal is generated. With reference to FIG. 2, this is accomplished by passing the measured impedance tissue signal through a high pass filter 29 and then pass the absolute value of the high pass through a low pass filter 30. The resulting filtered signal is the arc detection signal that is scaled and capped (for example by a 0 to 1 scale representing the level of arcing, where 1 represents heavy arcing and 0 represents no arcing). The arc detection signal rises as arcing increases and reduces and arcing decreases.

Arcing may also be detected by detecting rapid changes in the target control signal and/or by detecting rapid changes in either the voltage or current signals. If arcing is detected, the method proceeds to step 150 wherein the arc detection signal is used to make adjustments to the output control algorithm of the controller 24. This may be achieved by substituting the measured impedance signal with an average impedance value. By using the average impedance value to obtain the target control signal the generator 20 avoids using extreme impedance values associated with arcing. Alternatively, the output control algorithm may be configured to include selecting the target control signal associated with either the minimum or maximum impedance measured during arcing. This selects an impedance signal that is closest to the previously measured impedance ensuring that the impedance signal and, hence, the target control signal, do not deviate substantially from other values. Upon detecting arcing, the controller 24 may also stop and/or hold from issuing any target control signals thereby maintaining the output based on an immediately preceding measured impedance signal.

In response to arcing, RF generation may be stopped to quickly remove the arcing condition. This may be achieved to shutting down the RF output stage 28 and/or the MVPS 27. In addition, the circuit between the patient and generator 20 may be opened to prevent the RF energy from reaching tissue.

Other optimizations to the controller 24 are envisioned so that arcing is extinguished or energy delivery is enhanced during arcing. In particular, the calculations performed by the output control algorithm may be modified so that the desired output voltage, current and/or power are adjusted when arcing is present.

Further, modification to the waveform produced by the RF output stage 28 may be made in response to arcing. This may include momentary modification of the crest factor (i.e., ratio of the peak value to RMS value), the waveform and/or the duty cycle of the waveform. Adjustments to the crest factor and the duty cycle enhance or extinguish the arc. Low duty cycles tend to provide coagulation behavior whereas high duty cycles tend to provide for better cutting behavior. Thus, momentarily increasing the duty cycle of the waveform extinguishes the arc. Other ways of providing arc-based adaptive control include adjusting PID gain of the controller 24 such that the gain is reduced as the level of arcing increases.

In step 160, after the arcing conditions are removed, the modifications made to the controller 24 and/or the waveform are recalibrated and normal operating conditions are restored.

The arc-based adaptive control method according to the present disclosure allows for fast response to changes in non-arcing conditions and slows down the controller 24 during arcing so that the controller may readily select an alternate output value for heating a particular tissue type. This limits aggressive arcing behavior (e.g., so called entry/exit sparking). Another recognizable advantage is that electrosurgical systems utilizing arc-based control methods are capable of automatically switching from cutting to coagulation mode. Thus, during low arcing conditions, the system is optimized for cutting, but as the arcing increases the system adjusts so that coagulation is enhanced.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for controlling an electrosurgical generator, the method comprising the steps of:
   outputting electrosurgical energy;
   measuring impedance to obtain at least one measured impedance signal;
   filtering the at least one measured impedance signal to detect an arcing condition; and
   adjusting a PID gain of a controller of the electrosurgical generator to adjust the output of electrosurgical energy in response to the detected arcing condition without terminating the output of electrosurgical energy.

2. A method according to claim 1, wherein adjusting the output of electrosurgical energy includes adjusting a crest factor of the electrosurgical energy to enhance or extinguish the arcing condition.

3. A method according to claim 1, wherein adjusting the output of electrosurgical energy includes adjusting a duty cycle to enhance or extinguish the arcing condition.

4. A method according to claim 3, wherein adjusting the duty cycle includes increasing the duty cycle to extinguish the arcing condition.

5. A method according to claim 1, wherein adjusting the PID gain includes reducing the PID gain as a level of the detected arcing condition increases.

6. A method according to claim 1, wherein adjusting the output of electrosurgical energy includes adjusting at least one parameter of the electrosurgical energy selected from the group consisting of voltage, current, and power.

7. A method according to claim 1, wherein the electrosurgical energy is initially output at a first operating condition prior to detection of the arcing condition, the electrosurgical energy being output at a second operating condition during adjustment of the output of electrosurgical energy in response to the arcing condition, and the output of the electrosurgical energy returns to the first operating condition after the arcing condition has been extinguished.

8. A method according to claim 7, wherein when the electrosurgical generator is in the first operating condition the electrosurgical generator responds to non-arcing conditions at a first rate, and when in the second operating condition the electrosurgical generator responds to the arcing condition at a second rate, the second rate being slower than the first rate.

9. A method according to claim 1, further including generating at least one target control signal as a function of the at least one measured impedance signal, the at least one target control signal controlling the output of electrosurgical energy.

10. A method according to claim 9, wherein adjusting the output of electrosurgical energy includes substituting an average impedance value for the at least one measured impedance signal when generating the at least one target control signal.

11. A method according to claim 9, wherein adjusting the output of electrosurgical energy includes substituting a maximum impedance value measured during the arcing condition for the at least one measured impedance signal when generating the at least one target control signal.

12. A method according to claim 9, wherein adjusting the output of electrosurgical energy includes substituting a minimum impedance value measured during the arcing condition for the at least one measured impedance signal when generating the at least one target control signal.

13. A method according to claim 9, wherein adjusting the output of electrosurgical energy includes substituting an impedance value that was measured immediately preceding the arcing condition for the at least one measured impedance signal when generating the at least one target control signal.

14. A method for controlling an electrosurgical generator, the method comprising the steps of:
- outputting electrosurgical energy;
- measuring impedance to obtain at least one measured impedance signal;
- filtering the at least one measured impedance signal to detect an arcing condition;
- substituting a maximum impedance value measured during the arcing condition for the at least one measured impedance signal;
- adjusting the output of electrosurgical energy in response to the detected arcing condition without terminating the output of electrosurgical energy; and
- generating at least one target control signal as a function of the at least one measured impedance signal, the at least one target control signal controlling the output of electrosurgical energy.

* * * * *